United States Patent
Martinez Gil et al.

(10) Patent No.: US 11,912,678 B2
(45) Date of Patent: Feb. 27, 2024

(54) LRRK2 INHIBITING COMPOUNDS AND USE THEREOF FOR TREATING NEURODEGENERATIVE DISEASES

(71) Applicant: CONSEJO SUPERIOR DE INVESTIGACIONES CIENTÍFICAS, Madrid (ES)

(72) Inventors: Ana Martinez Gil, Madrid (ES); Carmen Gil Ayuso-Gontan, Madrid (ES); Josefa Zaldivar Diaz De Bonilla, Madrid (ES); Rocio Benitez Fernandez, Madrid (ES)

(73) Assignee: CONSEJO SUPERIOR DE INVESTIGACIONES CIENTÍFICAS, Madrid (ES)

( * ) Notice: Subject to any disclaimer, the term of this patent is extended or adjusted under 35 U.S.C. 154(b) by 552 days.

(21) Appl. No.: 17/270,236

(22) PCT Filed: Aug. 8, 2019

(86) PCT No.: PCT/ES2019/070557
§ 371 (c)(1),
(2) Date: Feb. 22, 2021

(87) PCT Pub. No.: WO2020/039110
PCT Pub. Date: Feb. 27, 2020

(65) Prior Publication Data
US 2021/0323936 A1   Oct. 21, 2021

(30) Foreign Application Priority Data
Aug. 24, 2018   (ES) ................ ES201830841

(51) Int. Cl.
*C07D 277/80*   (2006.01)
*A61K 45/06*    (2006.01)
*A61P 25/28*    (2006.01)

(52) U.S. Cl.
CPC ............ *C07D 277/80* (2013.01); *A61K 45/06* (2013.01); *A61P 25/28* (2018.01)

(58) Field of Classification Search
CPC ............................... C07D 277/80; A61P 25/28
See application file for complete search history.

(56) References Cited

FOREIGN PATENT DOCUMENTS

| WO | WO-2004078115 A2 * | 9/2004 | ........... A61K 31/428 |
|----|---------------------|--------|------------------------|
| WO | 2006038039 A1       | 4/2006 |                        |
| WO | 2010077068 A2       | 7/2010 |                        |
| WO | 2011141756 A1       | 11/2011|                        |
| WO | 2013139882 A1       | 9/2013 |                        |
| WO | 2015118026 A1       | 8/2015 |                        |

OTHER PUBLICATIONS

Aurora Fine Chemicals. Product No. 179.329.291. Chemazone Online Chemical Services. pp. 1-3 (Year: 2012).*

Morales-Garcia et al., "Biological and Pharmacological Characterization of Benzothiazole-Based CK-1δ Inhibitors in Models of Parkinson's Disease", ACS Omega, The American Chemical Society, vol. 2, Issue 8, 2017, pp. 5215-5220, 13 pages.

Nosova et al., "Fluoro-containing Heterocycles: XIII. Fluoro-containing Derivatives of Thiazolo[3,2-a]-, Benzothiazolo [3,2-a]-, and Benzimidazo [3,2-a]quinazolinones", Springer Link, Russian Journal of Organic Chemistry, vol. 41, Issue 11, 2005, pp. 1671-1677, 7 pages.

Crivori et al., "Predicting Blood-Brain Barrier Permeation from Three-Dimensional Molecular Structure", Journal Medicinal Chemistry, American Chemical Society, vol. 43, 2000, pp. 2204-2216, 13 pages.

Di et al., "High throughput artificial membrane permeability assay for blood-brain barrier", Elsevier, Science Direct, European Journal of Medicinal Chemistry, vol. 38, 2003, pp. 223-232, 10 pages.

* cited by examiner

*Primary Examiner* — Kortney L. Klinkel
*Assistant Examiner* — Richard Grant Peckham
(74) *Attorney, Agent, or Firm* — Hayes Soloway PC

(57) ABSTRACT

The present invention relates to a series of compounds having a structural benzothiazole-benzamide core with capacity to inhibit the LRRK2 enzyme, due to which the invention also relates to the use of these compounds for treating neurodegenerative diseases in which this enzyme is involved, such as Parkinson's Disease or Alzheimer's Disease.

14 Claims, 2 Drawing Sheets

LRRK2 INHIBITING COMPOUNDS AND USE THEREOF FOR TREATING NEURODEGENERATIVE DISEASES

CROSS-REFERENCE TO RELATED APPLICATIONS AND PRIORITY

This patent application claims priority from PCT Patent Application No. PCT/ES2019/070557 filed Aug. 8, 2019, which claims priority from Spanish Patent Application No. P201830841 filed Aug. 24, 2018. Each of these patent applications are herein incorporated by reference in their entirety.

The present invention relates to a series of compounds having a structural benzothiazole-benzamide core with capacity to inhibit the LRRK2 enzyme and are therefore useful in the treatment of neurodegenerative diseases in which this enzyme is involved, such as Parkinson's Disease or Alzheimer's Disease.

BACKGROUND OF THE INVENTION

The increased incidence of neurodegenerative diseases due to higher life expectancy in current society has made the search for treatments of these diseases a priority. A common characteristic of people affected by any of these pathologies is the progressive loss of neurons in specific regions of the nervous system and the ensuing deterioration of cognitive and motor functions. Considering the still unknown aetiology and absence of effective treatments, the discovery of therapeutically effective targets is required.

It is well known that in certain pathologies of the central nervous system (CNS) the hyperphosphorylated tau protein becomes aggregated and forms neurofibrillary tangles in the neurons, thereby causing the disintegration of the microtubules. However, the mechanism that causes this situation is not fully known. The possible kinases involved in this process are targets that are common in some proposed treatments, such as for example Dyrk1A, for which inhibitors that are potential drugs for treating so-called tauopathies have been described (WO2015/118026).

LRRK2 is an especially large protein which has been classified as a member of the ROCO superfamily (Ras-like GTPase). The physiological role of LRRK2 is not yet well determined and many of its substrates are unknown, but it has become an interesting target for neurodegenerative diseases, especially Parkinson's Disease. Additionally, it is considered that LRRK2 may be related to other pathologies in which the tau protein is affected, in addition to the inflammatory response, oxidative stress, synaptic and mitochondrial dysfunctions and neurogenesis in adults through the Wnt signaling pathway.

LRRK2 is abundantly expressed in microglia as well as in neurons, having demonstrated that it is a positive modulator of inflammation in murine microglia and that mutations in LRRK2 can alter the brain microenvironment, favouring neuroinflammation. Therefore, it can be related to various neurodegenerative diseases that cause neuroinflammation, such as, for example, Alzheimer's Disease, Parkinson's Disease, multiple sclerosis and amyotrophic lateral sclerosis, wherein their inhibitors play a neuroprotective role in reducing the inflammatory response. Additionally, LRRK2 increases GSK-3 enzyme activity and, therefore, promotes the hyperphosphorylation of the tau protein and other pathological proteins such as TDP-43. This known relationship makes it possible to establish which of the compounds that inhibit the activity of LRRK2 indirectly reduce the phosphorylation of tau and TDP-43, due to which LRRK2 inhibitors may be useful for treating tautopathies such as, for example, Alzheimer's Disease, progressive supranuclear palsy, frontotemporal dementia, Pick's Disease, etc., and diseases associated with TDP-43 such as amyotrophic lateral sclerosis, frontotemporal dementia and Alzheimer's Disease, among others.

Taking into account the interest of LRRK2 as a therapeutic target for neurodegenerative diseases, various inhibitors of this enzyme that would be potential treatments have been described (such as, for example, in WO2013/139882 and WO2011/141756). However, most of these compounds have the difficulty of not penetrating the blood-brain barrier (BBB) or of not being selective against other kinase proteins, which is a problem in molecules that are drug candidates for treating diseases of the CNS.

Therefore, since there is a need for advantageous therapeutic agents, the design and synthesis of molecules which are selective of the LRRK2 protein, capable of penetrating the CNS for treating neurodegenerative diseases is of vital importance.

DESCRIPTION OF THE INVENTION

The present invention relates to a series of compounds with a structural benzothiazole-benzamide core characteristically having a morpholine substituent, hereinafter, compounds of the invention. These structural factors convert them into selective inhibitors of the LRRK2 protein, which is involved in signaling pathways which are deteriorated in neurodegenerative diseases. Additionally, the compounds of the present invention are capable of penetrating the blood-brain barrier (BBB), as will be shown in the examples provided below. Therefore, in a first aspect, the present invention relates to a compound of formula (I):

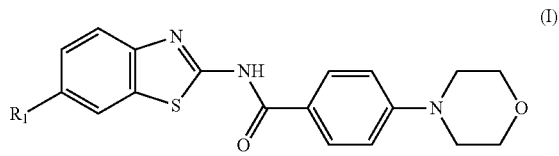

wherein $R_1$ is selected from H, $C_1$-$C_6$ alkyl, halogen, $CF_3$, —O—$C_1$-$C_6$ alkyl.

In a preferred embodiment of the compound (I), $R_1$ is H.

In another preferred embodiment of the compound (I), $R_1$ is a $C_1$-$C_4$ alkyl. In a more preferred embodiment of the compound (I), $R_1$ is selected from methyl or isopropyl.

In another preferred embodiment of the compound (I), $R_1$ is selected from F, Cl or Br.

In another preferred embodiment of the compound (I), $R_1$ is a —O—$C_1$-$C_4$ alkyl. In a more preferred embodiment of the compound (I), $R_1$ is selected from —O-methyl, —O-ethyl and —O— propyl.

In another preferred embodiment of the compound (I), $R_1$ is $CF_3$.

In another preferred embodiment, the compound of formula (I) is selected from the following list:
N-(benzothiazole-2-yl)-4-morpholinobenzamide,
N-(6-methoxybenzothiazole-2-yl)-4-morpholinobenzamide,
N-(6-trifluoromethylbenzothiazole-2-yl)-4-morpholinobenzamide,
N-(6-methylbenzothiazole-2-yl)-4-morpholinobenzamide,
N-(6-chlorobenzothiazole-2-yl)-4-morpholinobenzamide, N-(6-fluorobenzothiazole-2-yl)-4-morpholinobenzamide,
N-(6-ethoxybenzothiazole-2-yl)-4-morpholinobenzamide,
N-(6-bromobenzothiazole-2-yl)-4-morpholinobenzamide,
N-(6-propoxybenzothiazole-2-yl)-4-morpholinobenzamide,
N-(6-isopropylbenzothiazole-2-yl)-4-morpholinobenzamide.

In the present invention, the term "$C_1$-$C_6$ alkyl" relates to an aliphatic, linear or branched chain radical, having 1 to 6 carbon atoms, preferably between 1 and 4 carbon atoms such as, for example, but not limited to, methyl, ethyl, n-propyl, i-propyl, n-butyl, terc-butyl, sec-butyl, n-pentyl, n-hexyl. The alkyl group may optionally be substituted by one or more substituents such as halogen, hydroxyl, —O—$C_1$-$C_6$ alkyl, —CO—$C_1$-$C_6$ alkyl, —CN, —COOH, —COO—$C_1$-$C_6$ alkyl, —CONH—$C_1$-$C_6$ alkyl or —$SO_2$—$C_1$-$C_6$ alkyl.

The term "halogen" relates, in the present invention, to fluoride, bromine, chlorine or iodine.

The present invention also relates to isomers of the compounds of formula (I). The term "isomers" is understood to be chemical compounds having the same number and type of atoms as another chemical species, but with different arrangement or orientation, and relates to functional isomers, structural isomers, tautomers, valence isomers or stereoisomers.

Another aspect of the invention is the compound of formula (I) as described earlier for use as a medicament.

Another aspect of the invention relates to the previously described compound of formula (I) for use in the treatment of a neurodegenerative disease which may be a synucleinopathy or a tauopathy.

Synuclein is a presynaptic protein whose physiological role is undetermined and is thought to be involved in synaptic plasticity processes. It abounds in brain tissue and the conformational and biochemical changes suffered by this protein determine cytoplasmatic inclusions that characterise various neurodegenerative disorders, including Parkinson's Disease, dementia with Lewy bodies or multiple system atrophy, grouped under the term synucleinopathies.

The set of diseases known as tauopathies derives from the neuropathological study of different neurodegenerative diseases with intraneuronal aggregates of tau protein. Tauopathies include, namely, Alzheimer's Disease, progressive supranuclear palsy or frontotemporal lobar degeneration complex.

In a preferred embodiment of the use of the compound of formula (I), the neurodegenerative disease is selected from Alzheimer's Disease, Parkinson's Disease, Pick's Disease, progressive supranuclear palsy, corticobasal degeneration, frontotemporal dementia, parkinsonism linked to chromosome 17, argyrophilic dementia, post-encephalitic parkinsonism and primary age-related tauopathy.

In a more preferred embodiment of the use of the compound of formula (I), the neurodegenerative disease is Parkinson's Disease.

In another more preferred embodiment of the use of the compound of formula (I), the neurodegenerative disease is Alzheimer's Disease.

Another aspect of the invention relates to a pharmaceutical composition comprising a compound of formula (I) as described earlier, and optionally a pharmaceutically acceptable carrier or excipient.

In a preferred embodiment, said pharmaceutical composition also comprises another active ingredient.

The compounds of the invention, in the therapeutic use thereof or forming part of a pharmaceutical composition, may be in crystalline form as free compounds or as solvates and both forms are intended to fall within the scope of the present invention. In this regard, the term "solvate", as used herein, includes both pharmaceutically acceptable solvates, i.e., solvates of the compound of formula (I) which may be used in the preparation of a drug, and pharmaceutically non-acceptable solvates, which may be useful in the preparation of pharmaceutically acceptable solvates or salts. The nature of the pharmaceutically acceptable solvate is not critical provided that it is pharmaceutically acceptable. In a particular embodiment, the solvate is a hydrate. Solvates can be obtained by conventional solvation methods well known to persons skilled in the art.

The compounds of formula (I) for therapeutic use or forming part of a pharmaceutical composition are prepared in solid form or aqueous suspension, in a pharmaceutically acceptable diluent. These preparations can be administered via any appropriate route of administration, to which end said preparation will be formulated in the pharmaceutical form adequate to the chosen route of administration. In a particular embodiment, the route of administration of the compound of formula (I) provided by this invention is oral, topical, rectal or parenteral (including subcutaneous, intraperitoneal, intradermal, intramuscular, intravenous, etc.). A review of the different pharmaceutical forms of the administration of drugs and of the necessary excipients to obtain them can be found, for example, in the "Treatise on Galenic Pharmacy", C. Faulí i Trillo, 1993, Luzán 5, S. A. Ediciones, Madrid, or in other regular or similar literature of Spanish and US Pharmacopoeias.

The compounds described in the present invention, their pharmaceutically acceptable salts, solvates and the pharmaceutical compositions containing them can be used together with other additional drugs to provide combination therapy. Said additional drugs may form part of the same pharmaceutical composition or, alternatively, may be provided in the form of a separate composition for the simultaneous or non-simultaneous administration of the pharmaceutical composition comprising a compound of formula (I), or a pharmaceutically acceptable salt, stereoisomer or solvate thereof.

Unless indicated otherwise, the compounds of the invention may also include compounds that differ only in the presence of one or more isotopically enriched atoms. For example, compounds having said structure, with the exception of the substitution of one hydrogen atom for one deuterium or tritium atom, or the substitution of one carbon atom for one $^{13}C$ or $^{14}C$-enriched carbon atom or one $^{15}N$-enriched nitrogen atom, fall within the scope of this invention.

Throughout the description and the claims, the word "comprises" and its variants do not intend to exclude other technical features, additives, components or steps. For persons skilled in the art, other objects, advantages and features of the invention shall be partly inferred from the description and partly from the practice of the invention. The following examples and figures are provided by way of illustration and are not intended to limit the present invention.

EXAMPLES

Figure 1:
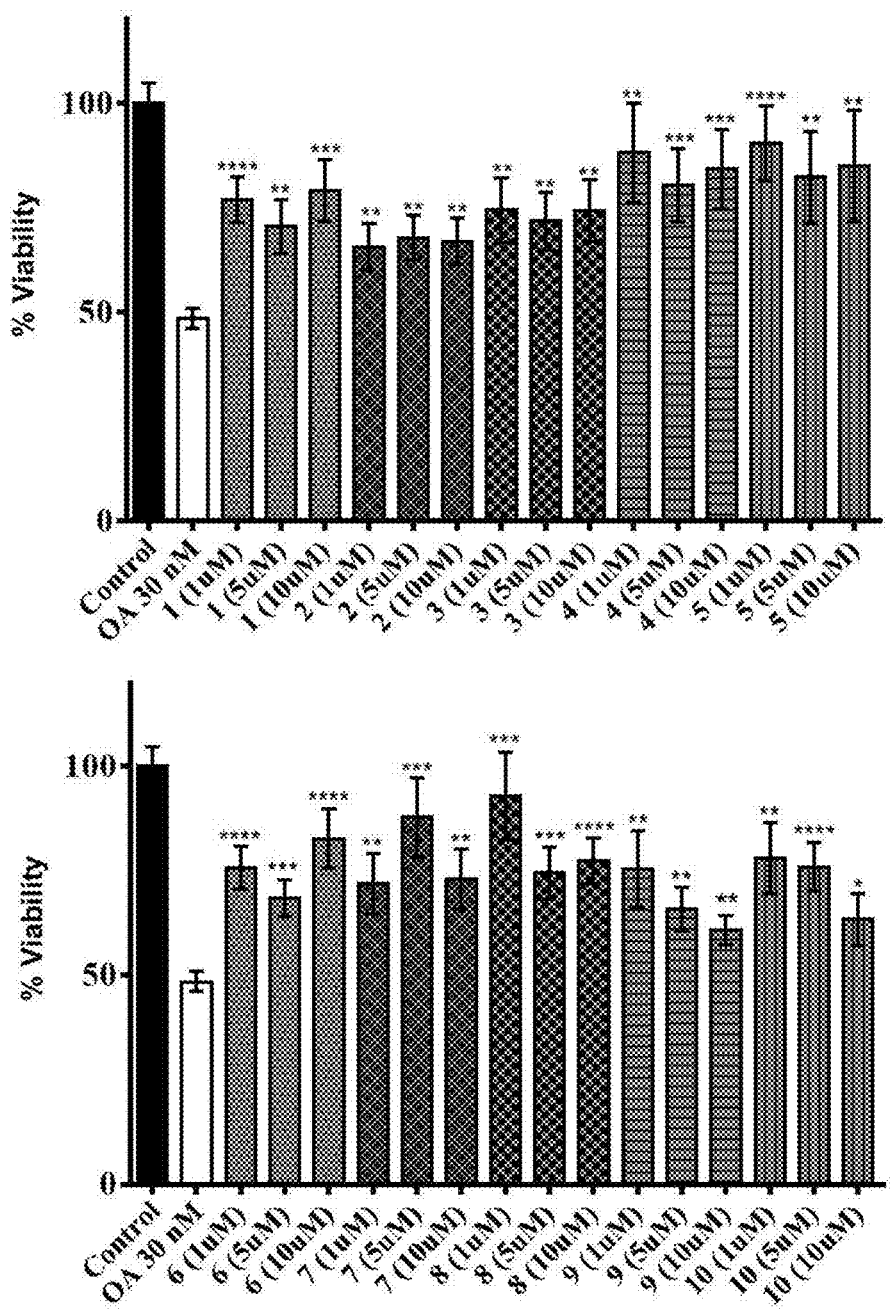
FIG. 1. Shows neuroprotection against the hyperphosphorylation of tau of LRRK2 inhibiting compounds 1-10 of the invention.

The invention is illustrated below by means of assays performed by the inventors, which demonstrates the effectiveness of the product of the invention.

Example 1. Synthesis and Characterisation of the Compounds of the Invention

N-(benzothiazole-2-yl)-4-morpholinobenzamide (1)

276.0 mg of 4-morpholinobenzoic acid (1.3 mmol), 331.00 mg of EDCl (1.4 mmol), 24.4 mg of DMAP (0.3 mmol) and 335 µL (2.4 mmol) of triethylamine were dissolved in dichloromethane. After stirring for 1 hour at room temperature, 200 mg of 2-aminobenzothiazole (1.3 mmol) were added. The reaction is left under stirring at room temperature during the night. After this time period the crude was washed with saturated solutions of $NaHCO_3$ and NaCl, respectively. Next, the organic phase is dried on anhydrous magnesium sulfate, the solvent is evaporated at low pressure and is purified by chromatography in a flash column using a mixture of eluents $CH_2Cl_2$/MeOH (20:1) to obtain a yellow solid (72 mg, 16%). HPLC Purity >95%. MS: m/z 340 [M+1]+. $^1$H NMR (300 MHz, $CDCl_3$) δ 10.21 (s, 1H, NH), 7.90 (d, J=9.0 Hz, 2H), 7.84 (dd, J=8.5, 1.5 Hz, 1H), 7.62 (dd, J=8.3, 1.2 Hz, 1H), 7.44-7.35 (m, 1H), 7.35-7.27 (m, 1H), 4.01-3.71 (m, 4H), 3.49-3.16 (m, 4H). $^{13}$C NMR (75 MHz, DMSO-$d_6$) δ 164.6, 159.1, 154.3, 148.2, 132.2, 129.4, 126.0, 123.7, 121.3, 121.1, 120.7, 113.8, 66.5, 47.4.

N-(6-methoxybenzothiazole-2-yl)-4-morpholinobenzamide (2)

230.0 mg of 4-morpholinobenzoic acid (1.1 mmol), 276.6 mg of EDCl (1.4 mmol), 24.43 mg of DMAP (0.2 mmol) and 248 µL (1.7 mmol) of triethylamine were dissolved in dichloromethane. After stirring for 1 hour at room temperature, 200 mg of 2-amino-6-methoxybenzothiazole (1.1 mmol) were added. The reaction is left under stirring at room temperature during the night. After this time period the crude was washed with saturated solutions of $NaHCO_3$ and NaCl, respectively. Next, the organic phase is dried on anhydrous magnesium sulfate, the solvent is evaporated at low pressure and is purified by flash column chromatography using a mixture of eluents $CH_2Cl_2$/MeOH (50:1) to obtain a yellow solid (36 mg, 9%). P.f.: 237.6-240.0° C. HPLC Purity: 95%. MS: m/z 370 [M+H]+. $^1$H NMR (300 MHz, $CDCl_3$) δ 9.47 (s, 1H), 7.88 (d, J=9.0 Hz, 2H), 7.64 (d, J=8.8 Hz, 1H), 7.33 (d, J=2.6 Hz, 1H), 7.04 (dd, J=8.8, 2.6 Hz, 1H), 6.94 (d, J=9.0 Hz, 2H), 3.93-3.83 (m, 7H), 3.36-3.31 (m, 4H). $^{13}$C NMR (75 MHz, DMSO-$d_6$) δ 164.8, 156.9, 156.0, 153.8, 142.7, 132.8, 129.8, 120.8, 120.5, 114.80, 113.1, 104.6, 65.8, 55.6, 46.8.

N-(6-trifluoromethylbenzothiazole-2-yl)-4-morpholinobenzamide (3)

189.9 mg of 4-morpholinobenzoic acid (0.9 mmol), 228.53 mg of EDCl (1.2 mmol), 22.41 mg of DMAP (0.2 mmol) and 223 µL (1.5 mmol) of triethylamine were dissolved in dichloromethane. After stirring for 1 hour at room temperature, 200 mg of 2-amino-6-trifluorobenzothiazole (0.9 mmol) were added. The reaction is left under stirring at room temperature during the night. After this time period the crude was washed with saturated solutions of $NaHCO_3$ and NaCl, respectively. Next, the organic phase is dried on anhydrous magnesium sulfate, the solvent is evaporated at low pressure and is purified by automatic flash column chromatography (Biotage®Isolera One) using a mixture of eluents hexane/AcOEt to obtain a yellow solid (79 mg, 26%). P.f.: 218.5-218.5° C. HPLC Purity: 95%. MS: m/z 408 [M+H]+. $^1$H NMR (300 MHz, $CDCl_3$) δ 10.85 (s, 1H), 8.13 (s, 1H), 7.89 (d, J=9.0 Hz, 1H), 7.57-7.53 (m, 2H), 6.84 (d, J=9.0 Hz, 2H), 3.87-3.83 (m, 4H), 3.31-3.26 (m, 4H). $^{13}$C NMR (75 MHz, $CDCl_3$) δ 163.8, 160.8, 153.4, 149.4, 131.2, 128.5, 124.9 (d, J=32.5 Hz), 124.3, 122.1 (d, J=3.4 Hz), 119.6 (d, J=32.2 Hz), 118.0 (d, J=4.2 Hz), 112.7, 65.4, 46.3, 28.6. $C_{19}H_{16}F_3N_3O_2S$: Theoretical (%) C, 56.01; H, 3.96; N, 10.31; S, 7.87. Found (%) C, 56.13; H, 3.98; N, 10.38; S, 7.59.

N-(6-methylbenzothiazole-2-yl)-4-morpholinobenzamide (4)

252.4 mg of 4-morpholinobenzoic acid (1.2 mmol), 303.5 mg of EDCl (1.58 mmol), 20.06 mg of DMAP (0.2 mmol) and 272 µL (1.9 mmol) of triethylamine were dissolved in dichloromethane. After stirring for 1 hour at room temperature, 200 mg of 2-amino-6-methylbenzothiazole (1.2 mmol) were added. The reaction is left under stirring at room temperature during the night. After this time period the crude was washed with solutions of HCl (0.1M), saturated $NaHCO_3$ and saturated NaCl, respectively. Next, the organic phase is dried on anhydrous magnesium sulfate, the solvent is evaporated at low pressure and is purified by automatic flash column chromatography (Biotage®Isolera One) using a mixture of eluents hexane/AcOEt to obtain a yellow solid (43 mg, 10%). P.f.: 287.7-288.8° C. MS (ESI+): m/z 354 [M+H]+. $^1$H NMR (300 MHz, $CDCl_3$) δ 10.56 (s, 1H), 7.89 (d, J=8.9 Hz, 2H), 7.63 (s, 1H), 7.42 (d, J=8.3 Hz, 1H), 7.16 (dd, J=8.3, 1.7 Hz, 1H), 6.85 (d, J=8.9 Hz, 1H), 3.87-3.83 (m, 4H), 3.29-3.26 (m, 4H), 2.46 (s, 3H). $^{13}$C NMR (75 MHz, $CDCl_3$) δ 164.7, 158.5, 154.2, 146.1, 133.7, 132.3, 129.4, 127.5, 121.3, 121.1, 120.3, 113.8, 66.5, 47.5, 21.4. $C_{19}H_{19}N_3O_2S$: Theoretical (%) C, 64.57; H, 5.42; N, 11.89; S, 9.07. Found (%) C, 64.33; H, 5.38; N, 11.85; S, 8.96.

N-(6-chlorobenzothiazole-2-yl)-4-morpholinobenzamide (5)

224.4 mg of 4-morpholinobenzoic acid (1.1 mmol), 269.89 mg of EDCl (1.4 mmol), 26.4 mg of DMAP (0.2 mmol) and 242 µL (1.7 mmol) of triethylamine were dissolved in dichloromethane. After stirring for 1 hour at room temperature, 200 mg of 2-amino-6-chlorobenzothiazole (1.1 mmol) were added. The reaction is left under stirring at room temperature during the night. After this time period the crude was washed with solutions of HCl (0.1M), saturated $NaHCO_3$ and saturated NaCl, respectively. Next, the organic phase is dried on anhydrous magnesium sulfate, the solvent is evaporated at low pressure and is purified by automatic flash column chromatography (Biotage®Isolera One) using a mixture of eluents hexane/AcOEt to obtain a white solid (96 mg, 24%). P.f.: 245.4-246.4° C. HPLC Purity: 97%. MS: m/z 374 [M+H]+. $^1$H NMR (300 MHz, $CDCl_3$) δ 10.25 (s, 1H), 7.89 (d, J=8.9 Hz, 2H), 7.81 (d, J=2.1 Hz, 1H), 7.52 (d, J=8.7 Hz, 1H), 7.33 (dd, J=8.7, 2.1 Hz, 1H), 6.89 (d, J=9.0 Hz, 2H), 3.92-3.82 (m, 4H), 3.33-3.30 (m, 4H). $^{13}$C NMR (75 MHz, $CDCl_3$) δ 164.5, 159.3, 154.4, 146.8, 139.7, 133.5, 129.4, 126.7, 121.5, 121.0, 120.8, 113.7, 66.5, 47.4. $C_{18}H_{16}ClN_3O_2S$: Theoretical (%) C, 57.83; H, 4.31; N, 11.24; S, 8.58. Found (%) C, 57.56; H, 4.09; N, 11.43; S, 8.40.

N-(6-fluorobenzothiazole-2-yl)-4-morpholinobenzamide (6)

168.20 mg of 4-morpholinobenzoic acid (1.2 mmol), 296.3 mg of EDCl (1.5 mmol), 29.05 mg of DMAP (0.2 mmol) and 265 μL (1.9 mmol) of triethylamine were dissolved in dichloromethane. After stirring for 1 hour at room temperature, 200 mg of 2-amino-6-fluorobenzothiazole (1.2 mmol) were added. The reaction is left under stirring at room temperature during the night. After this time period the crude was washed with solutions of HCl (0.1M), saturated NaHCO$_3$ and saturated NaCl, respectively. Next, the organic phase is dried on anhydrous magnesium sulfate, the solvent is evaporated at low pressure and is purified by automatic flash column chromatography (Biotage®Isolera One) using a mixture of eluents hexane/AcOEt to obtain a white solid (79 mg, 19%). P.f.: 228.3-229.3° C. HPLC Purity: 98%. MS: m/z 358 [M+H]$^+$. $^1$H NMR (300 MHz, CDCl$_3$) δ 9.96 (s, 1H), 7.81 (d, J=8.9 Hz, 2H), 7.74 (d, J=2.1 Hz, 1H), 7.49 (d, J=8.6 Hz, 1H), 7.28 (dd, J=8.7, 2.1 Hz, 1H), 6.84 (d, J=8.7 Hz, 2H), 3.87-3.85 (m, 4H), 3.34-3.30 (m, 4H). $^{13}$C NMR (75 MHz, CDCl$_3$) δ 164.4, 159.2, 154.4, 147.0, 138.7, 133.6, 129.3, 126.8, 121.6, 121.0, 120.8, 113.8, 66.5, 47.4. C$_{18}$H$_{16}$FN$_3$O$_2$S: Theoretical (%) C, 60.49; H, 4.51; N, 11.76; S, 8.97. Found (%) C, 60.68; H, 4.50; N, 11.55; S, 8.72.

N-(6-ethoxybenzothiazole-2-yl)-4-morpholinobenzamide (7)

213.1 mg of 4-morpholinobenzoic acid (1.0 mmol), 256.2 mg of EDCl (1.3 mmol), 25.12 mg of DMAP (0.2 mmol) were dissolved in dichloromethane. After stirring for 6 hours at room temperature, 200 mg of 2-amino-6-ethoxybenzothiazole (1.0 mmol) and 229 μL of triethylamine (1.9 mmol) were added. The reaction is left under stirring at room temperature during the night. After this time period the crude was washed with solutions of HCl (0.1M), saturated NaHCO$_3$ and saturated NaCl, respectively. Next, the organic phase is dried on anhydrous magnesium sulfate, the solvent is evaporated at low pressure and is purified by automatic flash column chromatography (Biotage®Isolera One) using a mixture of eluents hexane/AcOEt to obtain a yellow solid (20 mg, 5%). P.f.: 222.8-223.8° C. HPLC Purity: 95%. MS: m/z 384 [M+H]$^+$. $^1$H NMR (300 MHz, CDCl$_3$) δ 8.07 (d, J=8.6 Hz, 2H), 7.54 (d, J=8.9 Hz, 1H), 7.35-7.18 (m, 1H), 7.04 (dd, J=8.9, 2.4 Hz, 1H), 6.89 (d, J=8.6 Hz, 2H), 4.07 (q, J=6.9 Hz, 2H), 3.89-3.69 (m, 4H), 3.38-3.25 (m, 4H), 1.43 (t, J=6.9 Hz, 3H). $^{13}$C NMR (75 MHz, CDCl$_3$) δ 164.4, 157.1, 156.0, 154.2, 142.3, 133.3, 129.3, 121.3, 121.2, 119.7, 115.5, 114.2, 113.8, 106.0, 104.9, 99.5, 66.5, 64.1, 64.1, 47.5, 14.8.

N-(6-bromobenzothiazole-2-yl)-4-morpholinobenzamide (8)

180.9 mg of 4-morpholinobenzoic acid (0.9 mmol), 217.6 mg of EDCl (1.1 mmol), 21.33 mg of DMAP (0.2 mmol) were dissolved in dichloromethane. After stirring for 6 hours at room temperature, 200 mg of 2-amino-6-bromobenzothiazole (0.9 mmol) and 195 μl of triethylamine (1.4 mmol) were added. The reaction is left under stirring at room temperature during the night. After this time period the crude was washed with solutions of HCl (0.1M), saturated NaHCO$_3$ and saturated NaCl, respectively. Next, the organic phase is dried on anhydrous magnesium sulfate, the solvent is evaporated at low pressure and is purified by automatic flash column chromatography (Biotage®Isolera One) using a mixture of eluents hexane/AcOEt to obtain a yellow solid (41 mg, 11%). P.f.: 237.5-238.5° C. HPLC Purity: 98%. MS: m/z 418 [M+H]+. $^1$H NMR (300 MHz, CDCl$_3$) δ 10.51 (s, 1H), 7.96 (s, 1H), 7.87 (d, J=9.0 Hz, 3H), 7.44 (dd, J=8.6, 1.9 Hz, 2H), 7.38 (d, J=8.6 Hz, 2H), 6.86 (d, J=9.0 Hz, 3H), 3.89-3.83 (m, 11H), 3.33-3.26 (m, 11H). $^{13}$C NMR (75 MHz, CDCl$_3$) δ 165.2, 160.4, 154.8, 147.1, 134.1, 130.0, 129.9, 124.3, 122.1, 121.1, 117.2, 114.1, 66.9, 47.8.

N-(6-propoxybenzothiazole-2-yl)-4-morpholinobenzamide (9)

248.8 mg of 4-morpholinobenzoic acid (1.2 mmol), 299.00 mg of EDCl (1.6 mmol), 29.3 mg of DMAP (0.2 mmol) were dissolved in dichloromethane. After stirring for 6 hours at room temperature, 250 mg of 2-amino-6-propoxybenzothiazole (1.2 mmol) and 267.6 μL (1.9 mmol) of triethylamine were added. The reaction is left under stirring at room temperature during the night. After this time period the crude was washed with a HCl solution (0.1M). Next, the organic phase is dried on anhydrous magnesium sulfate, the solvent is evaporated at low pressure and is purified by flash column chromatography using a mixture of eluents CH$_2$Cl$_2$/MeOH (50:1) to obtain a yellow solid (127 mg, 27%). HPLC Purity>95%. MS: m/z 398 [M+H]+. $^1$H NMR (300 MHz, CDCl$_3$) δ 7.88 (d, J=9.0 Hz, 2H), 7.46 (d, J=8.9 Hz, 1H), 7.31 (d, J=2.5 Hz, 1H), 6.96 (dd, J=8.9, 2.5 Hz, 1H), 6.88 (d, J=9.0 Hz, 2H), 3.98 (t, J=6.6 Hz, 2H), 3.89-3.83 (m, 4H), 3.32-3.27 (m, 4H), 1.85 (h, J=7.3 Hz, 2H), 1.06 (t, J=7.4 Hz, 2H). $^{13}$C NMR (75 MHz, CDCl$_3$) δ 163.6, 156.3, 155.2, 153.3, 141.27, 132.2, 128.4, 120.4, 120.3, 114.5, 112.8, 103.9, 69.2, 65.5, 46.5, 21.6, 9.5. C$_{21}$H$_{23}$N$_3$O$_3$S: Theoretical (%) C, 63.46; H, 5.83; N, 10.57; S, 8.07. Found (%) C, 63.73; H, 5.74, N, 10.09; S, 7.71.

N-(6-isopropylbenzothiazole-2-yl)-4-morpholinobenzamide (10)

269.4 mg of 4-morpholinobenzoic acid (1.3 mmol), 324.00 mg of EDCl (1.7 mmol), 32.00 mg of DMAP (0.3 mmol) were dissolved in dichloromethane. After stirring for 6 hours at room temperature, 250 mg of 2-amino-6-isopropylbenzothiazole (1.3 mmol) and 290.0 μL (2.1 mmol) of triethylamine were added. The reaction is left under stirring at room temperature during the night. After this time period the crude was washed with a HCl solution (0.1M). Next, the organic phase is dried on anhydrous magnesium sulfate, the solvent is evaporated at low pressure and is purified by flash column chromatography using a mixture of eluents CH$_2$Cl$_2$/MeOH (50:1) to obtain a yellow solid (218.4 mg, 44%). HPLC Purity>95%. MS: m/z 382 [M+H]+. $^1$H NMR (300 MHz, CDCl$_3$) δ 10.35 (s, 1H), 7.89 (d, J=9.0 Hz, 2H), 7.68 (d, J=1.7 Hz, 1H), 7.49 (d, J=8.4 Hz, 1H), 7.26-7.22 (m, 1H), 6.88 (d, J=9.0 Hz, 2H), 3.89-3.81 (m, 4H), 3.33-3.25 (m, 4H), 3.03 (p, J=6.9 Hz, 1H), 1.31 (d, J=6.9 Hz, 6H). $^{13}$C NMR (75 MHz, CDCl$_3$) δ 163.7, 157.7, 153.2, 145.3, 143.9, 131.3, 128.4, 124.0, 120.4, 119.4, 119.1, 117.5, 112.8, 65.5, 46.5, 33.2, 23.3. C$_{21}$H$_{23}$N$_3$O$_2$S: Theoretical (%) C, 66.12; H, 6.08; N, 11.00; S, 8.40. Found (%) C, 66.09; H, 6.13; N, 10.69; S, 8.54.

Example 2. Inhibition of LRRK2 and LRRK2 G2019S

The compounds were evaluated in LRRK2 and in the mutated form LRRK2 G2019S. This mutation is more frequent in the familial forms of Parkinson's Disease and has a significant increase in kinase activity. The experimental determination of the inhibition of both enzymes was carried out using the Adapta® method, which is an evaluation method of fluorescent kinase activity that determines ADP in a highly sensitive manner. The methodology can be divided into two stages: kinase reaction and ADP determination. In the first stage, all the components for the kinase reaction are added to the well and incubated for 60 min. After the reaction, the ADP detection solution which contains a Europium-labeled anti-ADP antibody (Alexa Fluor® 647 labeled ADP tracer) and EDTA, to stop the kinase reaction, are added to the reaction well. The ADP formed in the kinase reaction without inhibitor will displace the Alexa Fluor® 647 labeled ADP tracer of the antibody, resulting in the TR-FRET signal decrease. In the presence of the inhibitor, the amount of ADP formed is reduced, which does not modify the antibody-tracer interaction and, therefore, has a higher TR-FRET signal.

The assay is performed in 384-well plates. Adding 100 nL of the solution with the compound to be evaluated in 1% DMSO, 2.4 µL of HEPES solution, 2.5 µL of ATP solution, 4.5 µL of substrate solution. The 10 µl of the kinase reaction contain: 75-70 ng LRRK2 and 200 µM ERM (LRRKtide) in 25 mM Tris/7.5 mM HEPES pH 8.2, 0.005% BRIJ-35, 5 mM $MgCl_2$, 0.5 mM EGTA, 0.01% $NaN_3$ or 3-12 ng LRRK2 G2019S and 200 µM ERM (LRRKtide) in 25 mM Tris/7.5 mM HEPES pH 8.2, 0.005% BRIJ-35, 5 mM $MgCl_2$, 0.5 mM EGTA, 0.01% $NaN_3$. The plate is stirred for 30 s on a stirring plate and centrifuged for 1 min in a centrifuge at 1,000×g. The reaction is incubated at room temperature for 60 min. After this time period, 5 µL of the detection mixture is added, the plate is stirred for 30 s on a stirring plate and centrifuged for 1 min at 1,000×g. Fluorescence is determined in a plate reader and the data are analysed.

TABLE 1

Inhibition of LRRK2 and LRRK2 G2019S of heterocyclic compounds

| Compound No. | LRRK2 $IC_{50}$ (µM) | LRRK2 G2019S $IC_{50}$ (µM) |
|---|---|---|
| 1 | 0.696 | 0.360 |
| 2 | 0.368 | 0.108 |
| 3 | 1.060 | 0.293 |
| 4 | 0.523 | 0.332 |
| 5 | 0.777 | n.d. |
| 6 | 0.190 | 0.426 |
| 7 | 0.308 | 0.158 |
| 8 | 0.474 | 1.380 |
| 9 | 4.000 | 1.190 |
| 10 | 1.950 | 1.170 | n.d. not determined

Example 3. Neuroprotection Against Tau Hyperphosphorylation

The neuroprotective potential of the compounds was evaluated in an okadaic acid (OA)-induced neurodegeneration cell model. OA is an inhibitor of phosphatase 1 and 2 and is normally used to induce tau hyperphosphorylation in different cell lines. In this case, the human neuronal line SH-SY5Y is used. The cells are cultured in DMEM medium supplemented with 10% FBS and 1% penicillin/streptomycin at 37° C. and in an incubator with 5% $CO_2$. The SH-SY5Y cells are sown on a 96-well plate at a density of 60,000 cells per well for 48 hours. After this time period, the cells are pre-incubated with the compounds to be studied at a concentration of 1, 5 and 10 µM for 1 hour. After that time period, OA is added at a concentration of 30 nM, letting the plate incubate for a further 24 hours. Next, the cells were incubated with an MTT solution at 0.5 mg·mL$^{-1}$ for at least 4 hours at 37° C. and 5% $CO_2$. Next, the culture medium is removed and the formazan crystals joined to the base of the plate are dissolved with 200 µL of DMSO. Lastly, UV absorbance was measured at 595 nM in a plate reader (Varioskan Flash Microplate reader, Thermo Scientific). The neuroprotection results shown by the compounds studied (1, 2, 3, 4, 5, 6, 7, 8, 9 and 10) are shown in FIG. 1. In all cases, the treatment of the compounds prevents the damage caused by the okadaic acid and consequently phosphorylation of the tau protein. These data indicate that the compounds used are probably capable of reducing this phosphorylation and increasing neuronal viability, i.e. they protect the neurons in culture.

Example 4. Physico-Chemical Properties Compatible with the Blood-Brain Barrier Passage The physico-chemical properties of the synthesised compounds were determined using the LigPrep module and the QikProp tool, both of the Maestro® program (Maestro version 11.0.015 release 2016-4, Maestro, Schrödinger, LLC, New York, NY, 2016). Using these cheminformatics tools, the structures were prepared in a medium similar to the first physiological medium; and, once obtained, the physico-chemical properties were calculated. The physico-chemical properties of a compound are important to achieve therapeutic effectiveness, since they condition many of the processes of the ADME series (absorption, distribution, metabolism and excretion). Therefore, a prediction was made on the following features: the prediction of the blood-brain barrier passage (QP log BB), the polar surface area (PSA) and the octanol/water partition coefficient (QP log P o/w) (Table 2). According to these data, all the compounds fall within the adequate intervals; therefore, they all have good lipophilicity features, and capacity to form hydrogen bridges and penetrate the blood-brain barrier.

TABLE 2

Calculated physico-chemical properties: QPlogBB (brain/blood partition coefficient, interval (−3.0 to 1.2)); PSA (polar surface area, interval (7.0 to 200.0)); QPlogP o/w (octanol/water partition coefficient, interval (−2.0 to 6.5)).

| Compound | QPlogBB | PSA | QPLogP o/w |
|---|---|---|---|
| 1 | −0.156 | 63.022 | 3.112 |
| 2 | −0.235 | 71.307 | 2.910 |
| 3 | 0.100 | 63.025 | 4.084 |
| 4 | −0.177 | 63.023 | 3.150 |
| 5 | 0.004 | 63.020 | 3.599 |
| 6 | −0.047 | 63.020 | 3.345 |
| 7 | −0.337 | 70.765 | 3.635 |
| 8 | 0.014 | 63.020 | 3.674 |
| 9 | −0.420 | 70.765 | 3.997 |
| 10 | −0.265 | 63.024 | 4.060 |

Example 5. Permeability in the Central Nervous System (CNS) Using Parallel Artificial Membranes (PAMPA)

The permeability prediction of the different compounds on the central nervous system (CNS), blood-brain barrier passage, was determined using the parallel artificial membrane methodology (PAMPA) [Di, L.; Kerns, E. H.; Fan, K.; McConnell, O. J.; Carter, G. T. "High throughput artificial membrane permeability assay for blood-brain barrier" *Eur. J. Med. Chem.*, 2003, 38 (3), 223-232]. The above-referenced commercial compounds, phosphate buffer at pH=7.4 (PBS), Ethanol and dodecane were obtained from the commercial houses Sigma, Acros organics, Merck, Aldrich and Fluka, respectively. The pig brain lipid (catalogue reference 141101) was acquired at Avanti Polar Lipids. Both the 96-well donor plate (Multiscreen® IP Sterile Plate PVDF membrane, 0.45 μM pore size, catalogue reference MAIPS4510) and the 96-well acceptor plate (Multiscreen®, catalogue reference MAMCS9610) were acquired at Millipore. To filter the samples, PVDF membrane filters were used (30 mm diameter, 0.45 μm pore size) from the company Symta. The equipment used to measure UV absorbance in 96-well plates was a Thermoscientific Multiskan spectrum.

Figure 2:
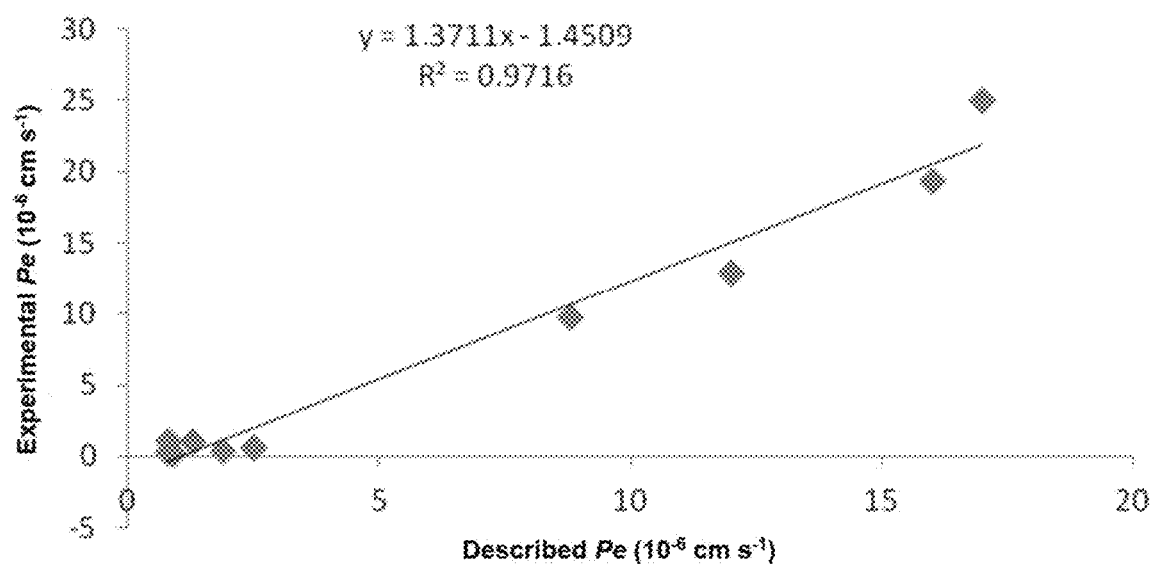
FIG. 2. Shows the linear correlation between the described and experimental permeability of ten commercial compounds using PAMPA-Blood-brain barrier methodology.

Ten reference compounds were selected, whose blood-brain barrier passage is known, in order to validate the experiment. Different amounts thereof were taken [(3-5 mg of caffeine, enoxacin, hydrocortisone, desipramine, ofloxacin, piroxicam, testosterone), (12 mg of promazine) and 25 mg of verapamil and atenolol], which were dissolved in ethanol (1,000 μl). 100 microlitres of these solutions were taken and 1,400 μL of EtOH and 3,500 μL of PBS phosphate buffer (pH=7.4) were added, in order to obtain a final concentration of EtOH of 30% in the solution. The solutions were filtered. Next, 180 μL of a PBS/EtOH (70/30) solution were added to each well of the acceptor plate. The donor plate was impregnated with 4 μL of a pig brain lipid solution dissolved in dodecane (20 mg mL$^{-1}$). After 5 minutes, 180 μL of solution of each compound were added on this plate. Of the compounds whose penetration in the central nervous system is being evaluated, between 1-2 mg were taken and dissolved in 1,500 μL of EtOH and 3,500 μL of PBS phosphate buffer (pH=7.4), filtered and added to the 96-well donor plate. Next, the donor plate was placed on top of the acceptor plate forming a kind of "sandwich" and left to incubate for 2 h and 30 min at 25° C. The passive transport compounds pass from the donor plate through the pig brain lipid to the acceptor plate. After 2 h and 30 min, the donor plate is carefully removed. The concentration and absorbance of both the commercial compounds and the synthesised derivatives that were evaluated in the acceptor and donor plates were determined using a UV absorbance reader. Each sample was analysed at 2 to 5 wavelengths, in at least three wells and in two independent experiments. The results are the average of the measurements [standard deviation (SD)] of the different experiments carried out. Ten reference commercial compounds whose penetration in the central nervous system is known were used in each experiment in order to validate the method. A good correlation was found between the experimental and described permeability (Pe) values, Pe (exptl)=1.3711 (desc)−1.4509 ($R^2$=0.972) (FIG. 2). Based on this equation and following the pattern described in the bibliography [Crivori, P.; Cruciani, G.; Testa, B. "Predicting Blood-Brain Barrier Permeation from Three-Dimensional Molecular Structure." *J. Med. Chem.*, 2000, 43, 2204-2216] for predicting the permeability of the blood-brain barrier, the compounds can be classified as permeable to the central nervous system (CNS) when they have a permeability >4.03×10$^{-6}$ cm s$^{-1}$. The results are shown in Table 3, where it can be observed how some of the evaluated compounds (1, 4, 6) are capable of penetrating the blood-brain barrier by passive diffusion.

TABLE 3

Permeability (Pe 10$^{-6}$ cm s$^{-1}$) in the PAMPA-Blood-brain barrier experiment for ten commercial compounds, used to validate the experiment, and different synthesised derivatives with their corresponding prediction of penetration in the central nervous system (CNS).

| Compound | Bibl.a | Pe (10−6 cm s−1)b | Prediction |
|---|---|---|---|
| Atenolol | 0.8 | 1.0 ± 0.6 | |
| Caffeine | 1.3 | 1.0 ± 0.8 | |
| Desipramine | 12 | 12.9 ± 0.4 | |
| Enoxacin | 0.9 | 0.2 ± 0.2 | |
| Hydrocortisone | 1.9 | 0.4 ± 0.1 | |
| Ofloxacin | 0.8 | 0.3 ± 0.3 | |
| Piroxicam | 2.5 | 0.6 ± 0.2 | |
| Promazine | 8.8 | 9.8 ± 0.5 | |
| Testosterone | 17 | 25.0 ± 0.2 | |
| Verapamil | 16 | 19.3 ± 0.7 | |
| 1 | | 13.4 ± 2.4 | CNS+ |
| 4 | | 19.0 ± 2.6 | CNS+ |
| 5 | | 3.42 ± 1.26 | CNS+/− |
| 6 | | 5.1 ± 0.1 | CNS+ |
| 9 | | 4.28 ± 3.45 | CNS+ |
| 10 | | 4.27 ± 2.7 | CNS+ | aReference Di et al *Eur. J. Med. Chem.*, 2003, 38 (3), 223-232.
bAverage data ± standard deviation (SD) of at least 2 independent experiments.

The invention claimed is:

1. A compound of formula (I):

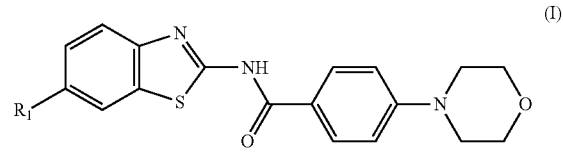

wherein $R_1$ is selected from H, $C_1$-$C_6$ alkyl, halogen, $CF_3$ and —O—$C_1$-$C_6$ alkyl.

2. The compound according to claim 1, wherein $R_1$ is H.

3. The compound according to claim 1, wherein $R_1$ is a $C_1$-$C_4$ alkyl.

4. The compound according to claim 3, wherein $R_1$ is selected from methyl or isopropyl.

5. The compound according to claim 1, wherein $R_1$ is selected from F, Cl or Br.

6. The compound according to claim 1, wherein $R_1$ is a —O—$C_1$-$C_4$ alkyl.

7. The compound according to claim 6, wherein $R_1$ is selected from —O-methyl, —O-ethyl and —O-propyl.

8. The compound according to claim 1, wherein $R_1$ is $CF_3$.

9. The compound according to claim 1, which is selected from the following list:
N-(benzothiazole-2-yl)-4-morpholinobenzamide,
N-(6-methoxybenzothiazole-2-yl)-4-morpholinobenzamide,
N-(6-trifluoromethylbenzothiazole-2-yl)-4-morpholinobenzamide,
N-(6-methylbenzothiazole-2-yl)-4-morpholinobenzamide,
N-(6-chlorobenzothiazole-2-yl)-4-morpholinobenzamide,
N-(6-fluorobenzothiazole-2-yl)-4-morpholinobenzamide,
N-(6-ethoxybenzothiazole-2-yl)-4-morpholinobenzamide,
N-(6-bromobenzothiazole-2-yl)-4-morpholinobenzamide,
N-(6-propoxybenzothiazole-2-yl)-4-morpholinobenzamide, N-(6-isopropylbenzothiazole-2-yl)-4-morpholinobenzamide.

10. A pharmaceutical composition comprising a compound of formula (I) according to claim 1.

11. The pharmaceutical composition according to claim 10, which further comprises another active ingredient.

12. A method of treatment of a neurodegenerative disease in a subject, comprising administering to said subject an effective amount of a compound of formula (I) according to claim 1, wherein the neurodegenerative disease is selected from Alzheimer's Disease, Parkinson's Disease, Pick's Disease, progressive supranuclear palsy, corticobasal degeneration, frontotemporal dementia, parkinsonism linked to chromosome 17, argyrophilic dementia, post-encephalitic parkinsonism and primary age-related tauopathy.

13. The method according to claim 12, wherein the neurodegenerative disease is Parkinson's Disease.

14. The method according to claim 12, wherein the neurodegenerative disease is Alzheimer's Disease.

* * * * *